United States Patent [19]

Silverman

[11] Patent Number: 5,405,842
[45] Date of Patent: Apr. 11, 1995

[54] TREATMENT OF STEROID DEPENDENT ASTHMATICS

[76] Inventor: Bernard A. Silverman, 1 Valencia Dr., Monsey, N.Y. 10952

[21] Appl. No.: 187,915

[22] Filed: Jan. 28, 1994

[51] Int. Cl.⁶ .................. A61K 31/57; A61K 31/63; A61K 31/615; A61K 31/44
[52] U.S. Cl. .................................. 514/171; 514/166; 514/352; 514/826
[58] Field of Search ................ 514/166, 171, 352, 826

[56] References Cited

U.S. PATENT DOCUMENTS

| | | | |
|---|---|---|---|
| 3,973,038 | 8/1976 | Umezawa et al. | 514/166 |
| 4,024,253 | 5/1977 | Umezawa et al. | 514/166 |
| 4,091,097 | 5/1978 | Umezawa et al. | 514/166 |
| 5,302,718 | 4/1994 | Agback et al. | 544/235 |

OTHER PUBLICATIONS

Derwent Abstract of Agback et al WO/PCT9310094 (May 27, 1993).
Merck Index 11th Ed. (1989) pp. 8917–8918 #8917 "Sulfasalazing".

*Primary Examiner*—Shep K. Rose
*Attorney, Agent, or Firm*—Israel Nissenbaum

[57] ABSTRACT

A method for the treatment of asthma, particularly corticosteroid dependent asthma with "steroid sparing" effect, but without serious toxicities prevalent with common "steroid sparing" treatments and medications, comprising the oral administration, in efficacious doses, of sulfasalazine (SSZ) (5-([p-(2-pyridylsulfamoyl) phenyl]azo) salicylic acid)

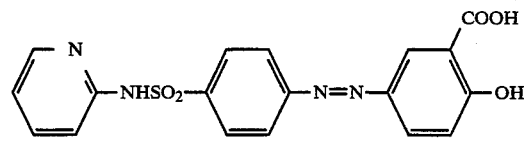

compounds having either the:

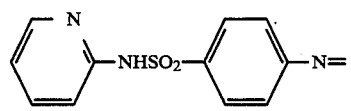

moiety, or the:

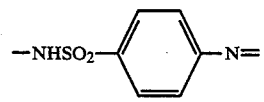

moiety. The SSZ and related compounds can be used as an adjuvant for corticosteroid treatments, which permits drastic reduction of the dosage levels of the corticosteroids with concomitant reduction of steroid side effects.

5 Claims, No Drawings

TREATMENT OF STEROID DEPENDENT ASTHMATICS

FIELD OF THE INVENTION

The present invention relates to the treatment of asthmatics, particularly corticosteroid dependent asthmatics and particularly to the use of "steroid sparing" medications with reduction of steroid side effects and toxicities.

BACKGROUND OF THE INVENTION

It is the consensus among almost all physicians that systemic and topical corticosteroids are usually required for the treatment of severe asthmatics. Systemic corticosteroids have significant anti inflammatory effects and, if given early enough to an asthmatic, they can effectively shorten the length and decrease the severity of acute asthma. However, when given over the long term for severe chronic asthma, such efficacy, for this condition, is accompanied by a long list of severe side effects, including cataracts, hypertension, diabetes, peptic ulcer, osteoporosis, poor wound healing, adrenal suppression, etc. Various drugs and treatments have been tried in order to provide an efficacious treatment while sparing the patient the effects of the corticosteroid treatment, i.e. "steroid sparing." However, such drugs have all demonstrated severe toxicities of their own and in many instances worse than that of corticosteroid treatments. In addition, these drug agents are potentially more toxic in children and pregnant or nursing women and are therefore inappropriate for the treatment of asthma in such patients.

SUMMARY OF THE INVENTION

It is an object of the present invention to provide an efficacious "steroid sparing" medication treatment for severe asthmatic conditions with reduced severity of side effects, and proven safety in children and pregnant women (category B).

It is a further object of the present invention to provide an adjuvant medication for use with corticosteroids whereby reduction of dosage, without contra indications, is possible, with reduced severity of side effects of the corticosteroids.

It is a still further object of the present invention to provide an efficacious medication treatment for severe asthmatic conditions with a compound having a long standing documented history of safe use (over 50 years) but for conditions other than for treatment of asthmatics.

These and other features and advantages of the present invention will become more evident from the following discussion.

DETAILED DESCRIPTION OF THE INVENTION

Generally the present invention comprises the treatment of severe asthmatic conditions with sulfasalazine (SSZ) (5 ([p (2 pyridylsulfamoyl) phenyl]azo) salicylic acid)

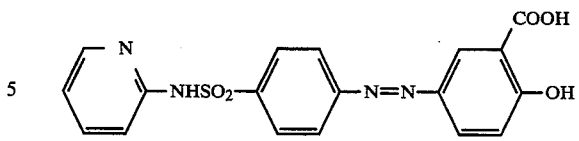

or other related compounds having either the anti inflammatory active moiety:

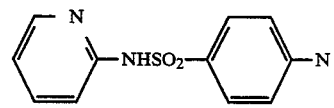

or the active moiety:

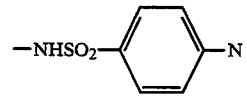

It has been discovered that SSZ can be effectively utilized as a sole asthma treating material, or, more preferably, as an adjuvant treating material, with corticosteroids, with reduction to half or less of the normal corticosteroid dosage treatments. When SSZ is used as an adjuvant material, in conjunction with the normal corticosteroid treating material, efficacy of the steroid treatment is maintained, despite the reduced dosage levels of the corticosteroids. Concomitant steroid side effects are similarly reduced.

A standard treatment for chronic asthma is treatment by administering Prednisone (a proprietary name for a common corticosteroid medication) in daily or every second day doses of 2.5 to 80 mg (for children, the maximum dosage is 1 to 2 mg/kg/day). In accordance with the present invention, daily oral doses of SSZ range from 1 4 grams, in solid or tablet form, divided into 2 to 4 doses. The child dose range of SSZ is 30 60 mg/day/kg, divided into 3 6 doses. With the adjuvant dosages of SSZ, Prednisone dosages can be cut to one sixth, or less, and number of courses of high dose treatment can be reduced by almost 90%, with concomitant reduction in severity of side effects, and without ill effects or reduction in efficacy of the treatment.

Another method of administering the SSZ could be by means of an atomizing inhalant, wherein minimal amounts, on the order of about one milligram, with such inhalant administration, reduce the dependency of asthmatics on corticosteroids.

SSZ is synthesized by the chemical linking of sulfapyridine and salicylic acid with an azo bond. Because of the antibacterial and anti inflammatory activity of its component moieties, it was initially administered for the treatment of rheumatoid arthritis (see U.S. Pat. No. 2,396,145). However, despite initial success in the treatment of rheumatoid arthritis, it fell out of favor with the development of cortisone. SSZ then was utilized, and has gained increasing favor as an agent for the treatment of inflammatory bowel disease for which its efficacy has been demonstrated and which is attributed to the 5 aminosalicylic acid moiety. However, the 5 aminosalicylic acid moiety alone has been recently proven to have this effect but with far fewer side effects and is commercially available. SSZ is also presently considered as an effective, though seldom used, second line agent in the treatment of rheumatoid arthritis, and there is evidence of efficacy in ankylosing spondylitis, reactive arthritis, and possibly juvenile rheumatoid arthritis. Its poor acceptance is attributable to its many side effects, leading to discontinuation in as many as 30% of patients, with gastrointestinal effects (e.g. anorexia, nausea, vomiting, gastric distress) as well as headaches and reversible oligospermia predominating. Other less frequent adverse reactions include skin rash, pruritis, urticaria, fever, Heinz body anemia, hemolytic anemia and cyanosis (occurring in about one of thirty patients). Despite such side effects, overall risk is far lower than that associated with the certain severe side effects of long term systemic corticosteroids.

Sulfazalazine has never been employed in the treatment of asthma. In fact its only therapeutic category listing is for the treatment of ulcerative colitis. It has only recently been discovered that asthma has an important inflammatory component which is pathologically very different from that of rheumatic or inflammatory bowel disease and is attributed mainly to the eosinophil and chemical mediators which attract it and are produced by it. Non steroidal anti-.inflammatory agents such as salicylates are generally ineffective and are known to actually be principal aggravating factors in many asthmatics, in particular, the severe, steroid dependent, "aspirin sensitive" group. The majority of asthmatics are atopic and thus are generally prone to various other allergic reactions and frequently to medication (sulfa containing drugs provide some of the highest rates of such allergic reactions). The first sentence under "PRECAUTIONS" in the 1993 Physician's Desk Reference description of azulfidine brand of sulfasalazine reads, "General: azulfidine should be given with caution to patients with severe allergy or bronchial asthma."

The steroid sparing effect of sulfasalazine may actually be due more to an immuno-suppressive effect (i.e., reduction in number and/or function of immunologic cells and their mediators) attributable primarily to the sulfapyridine moiety, rather than to an anti-inflammatory effect, analogous to other "non steroidal" agents,attributable to the 5 aminosalicylate moiety. This previously unrecognized effect could prove useful in the treatment of other allergic and immunologic disorders, i.e., in allergic rhinitis, atopic dermatitis, urticoria, autoimmune diseases (i.e. systemic lupus erythematosis, various connective tissue diseases, autoimmune thyroidiris, multiple sclerosis) as well as in the long term prevention of transplant graft rejection, all disorders where corticosteroids have been utilized and the "steroid sparing" effect would also apply.

In order to more clearly illustrate the efficacious utilization of the present invention in the treatment of asthma, the following example of actual patient treatment is presented.

EXAMPLE

A 46 year old female adult patient with corticosteroid dependent asthma was treated with SSZ. She began treatment and gradually reached a therapeutic dose of 1 gram, three times a day, one month later. Her average Prednisone dose over the seven months prior to starting SSZ was approximately 20 mg daily. Average Prednisone doses over the first four months of full dose SSZ treatment were reduced to just over 5 mg daily. Her highest dose during the period was 15 mg daily for 2 periods of 1 week. Prednisone dose over the eighteen months of SSZ treatment has averaged 3.5 mg daily. During the eighteen months the patient was treated with Prednisone, there were nine overall incidents wherein bursts were required. During the eighteen months after adjuvant treatment with SSZ there was only one occasion requiring a burst treatment. She experienced no clinical or laboratory side effects attributable to SSZ. Her asthma is generally better controlled, i.e., decreased symptoms and emergency visits and pulmonary function is improved overall. It is understood that the above discussion, with example of utilization is only illustrative of the present invention and that details contained therein are not to be construed as limitations on the present invention as defined in the following claims.

What is claimed is:

1. A method for the treatment of corticosteroid dependent asthma with "steroid sparing" effect, comprising the oral administration, in efficacious doses, of one or more compounds having the active moiety:

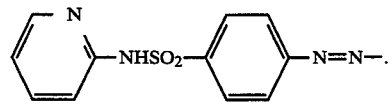

2. The method of claim 1, wherein the one or more compounds comprises sulfasalazine (5-([p-(2-pyridylsulamoyl) phenyl]azo) salicylic acid):

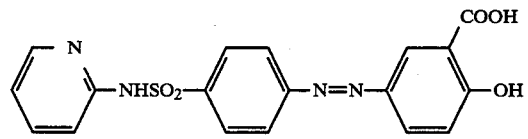

3. The method of claim 1, wherein said one or more compounds is utilized as an adjuvant with a corticosteroid compound having recognized utility in treatment of asthmatics.

4. The method of claim 3, wherein said one or more compounds is utilized in dosages of 1 to 4 grams per day and wherein dosages of corticosteroid compounds are reduced by at least half of normal dosage levels.

5. The method of claim 2, wherein said sulfazalazine is utilized as an adjuvant with prednisone.

* * * * *